United States Patent [19]
Meyer

[11] Patent Number: 5,895,662
[45] Date of Patent: Apr. 20, 1999

[54] MEAT PRODUCT PET MEDICINE CAPSULE

[76] Inventor: Martha C. Meyer, 8728 Nye Rd., Ventura, Calif. 93001

[21] Appl. No.: 09/001,722

[22] Filed: Dec. 31, 1997

[51] Int. Cl.⁶ .............................. A61K 9/00; A23L 1/31; A23K 1/18; B65D 39/00

[52] U.S. Cl. .................. 424/439; 426/140; 426/143; 426/92; 426/805; 215/14; 215/200; 215/296; 215/305; 215/371; 215/DIG. 3; 215/DIG. 4; D1/106; D1/199; D24/100

[58] Field of Search ...................... 424/451, 439, 424/442; 426/138, 140, 92, 132, 513–514, 516, 623, 641, 805, 282, 284, 143–44; D1/199, 106; D24/104; 215/14, 200, 296, 305, 371

[56] References Cited

U.S. PATENT DOCUMENTS 4,259,315  3/1981  Lippmann et al. .

*Primary Examiner*—Edward J. Webman

[57] ABSTRACT

A hollowed pet treat for medicating a pet is provided including a vial constructed entirely of an edible product and defining an interior space and an open top. Next provided is a cap formed entirely of the edible product for being removably coupled to the open top of the vial for containing a predetermined medicine within the interior space.

1 Claim, 2 Drawing Sheets

5,895,662

MEAT PRODUCT PET MEDICINE CAPSULE

BACKGROUND OF THE INVENTION

1. Field of the Invention

The present invention relates to pet medicine delivery systems and more particularly pertains to a meat product pet medicine capsule for administering various types of pet medicine to a dog or cat.

2. Description of the Prior Art

The use of pet medicine delivery systems is known in the prior art. More specifically, pet medicine delivery systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art pet medicine delivery systems include U.S. Pat. No. 4,857,333; U.S. Pat. No. 4,163,065; U.S. Pat. No. 4,220,152; U.S. Pat. No. 4,904,495; U.S. Pat. No. Design 254,337; and U.S. Pat. No. 5,270,064.

In these respects, the meat product pet medicine capsule according to the present invention substantially departs from the conventional concepts and designs of the prior art, and in so doing provides an apparatus primarily developed for the purpose of administering various types of pet medicine to a dog or cat.

SUMMARY OF THE INVENTION

In view of the foregoing disadvantages inherent in the known types of pet medicine delivery systems now present in the prior art, the present invention provides a meat product pet medicine capsule construction wherein the same can be utilized for administering various types of pet medicine to a dog or cat.

The general purpose of the present invention, which will be described subsequently in greater detail, is to provide a meat product pet medicine capsule apparatus and method which has many of the advantages of the pet medicine delivery systems mentioned heretofore and many novel features that result in a meat product pet medicine capsule which is not anticipated, rendered obvious, suggested, or even implied by any of the prior art pet medicine delivery systems, either alone or in any combination thereof.

To attain this, the present invention generally comprises a vial constructed entirely of an edible semi-rigid meat product. The vial has an upper extent with a hollow cylindrical configuration. As shown in FIG. 4, the vial includes a circular open top of a first diameter and a lower extent defined by a portion of a hollow sphere. The lower extent is integrally coupled in concentric relationship with the upper extent thus defining an interior space in communication with the open top. Next provided is a cap constructed entirely of the edible semi-rigid meat product, similar to the vial. The cap has a bottom with a solid cylindrical configuration having the first diameter. An intermediate portion of the cap is equipped with a solid cylindrical configuration and is integrally coupled in coaxial alignment with the bottom. The intermediate extent has a second diameter greater than the first diameter. A top defined by a portion of a solid sphere with the second diameter is integrally coupled to intermediate extent.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a meat product pet medicine capsule apparatus and method which has many of the advantages of the pet medicine delivery systems mentioned heretofore and many novel features that result in a meat product pet medicine capsule which is not anticipated, rendered obvious, suggested, or even implied by any of the prior art pet medicine delivery systems, either alone or in any combination thereof.

It is another object of the present invention to provide a meat product pet medicine capsule which may be easily and efficiently manufactured and marketed.

It is a further object of the present invention to provide a meat product pet medicine capsule which is of a durable and reliable construction.

An even further object of the present invention is to provide a meat product pet medicine capsule which is susceptible of a low cost of manufacture with regard to both materials and labor, and which accordingly is then susceptible of low prices of sale to the consuming public, thereby making such a meat product pet medicine capsule economically available to the buying public.

Still yet another object of the present invention is to provide a meat product pet medicine capsule which provides in the apparatuses and methods of the prior art some of the advantages thereof, while simultaneously overcoming some of the disadvantages normally associated therewith.

Still another object of the present invention is to provide a meat product pet medicine capsule for administering various types of pet medicine to a dog or cat.

Even still another object of the present invention is to provide a meat product pet medicine capsule that includes a vial constructed entirely of an edible product and defining an interior space and an open top. Next provided is a cap formed entirely of the edible product for being removably coupled to the open top of the vial for containing a predetermined medicine within the interior space.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
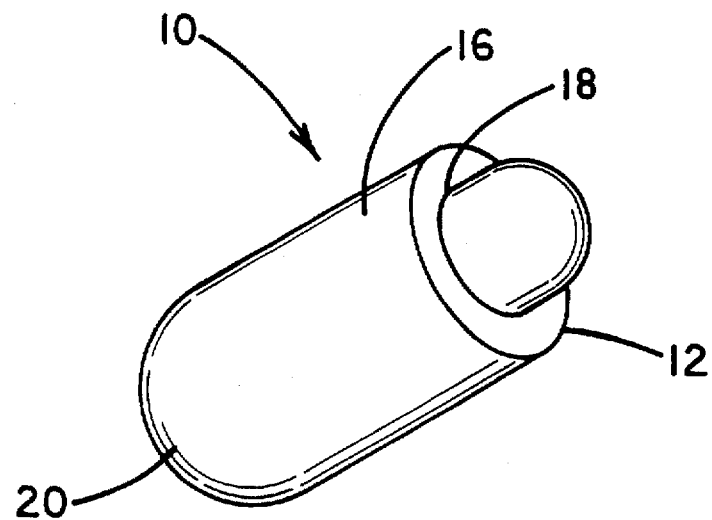
FIG. 1 is a perspective view of a meat product pet medicine capsule according to the present invention.
Figure 2:
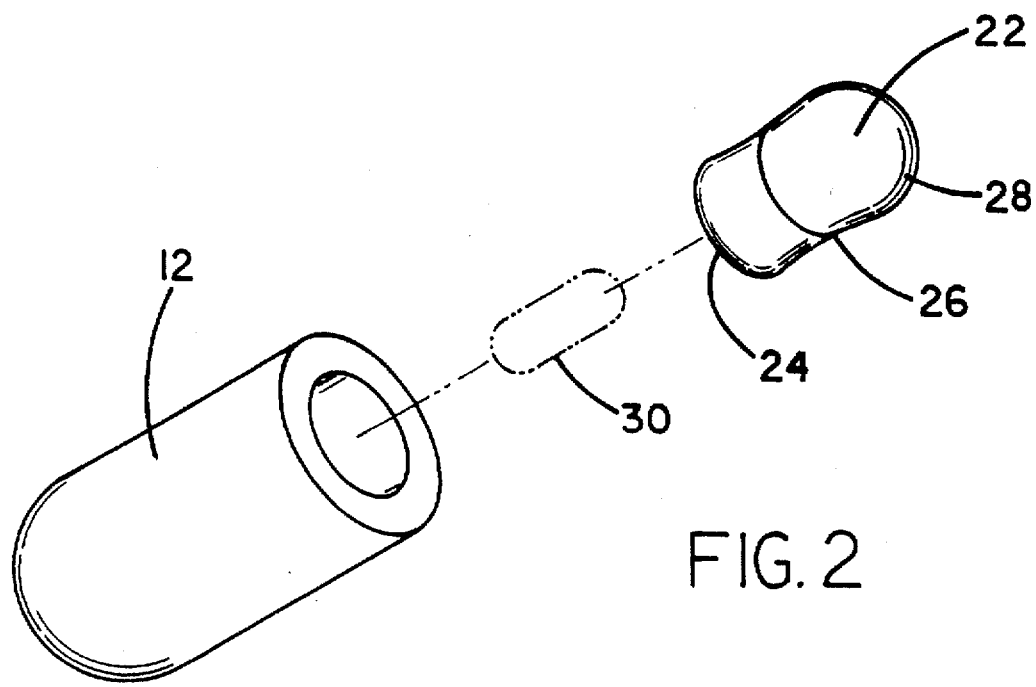
FIG. 2 is an exploded view of the present invention.
Figure 3:
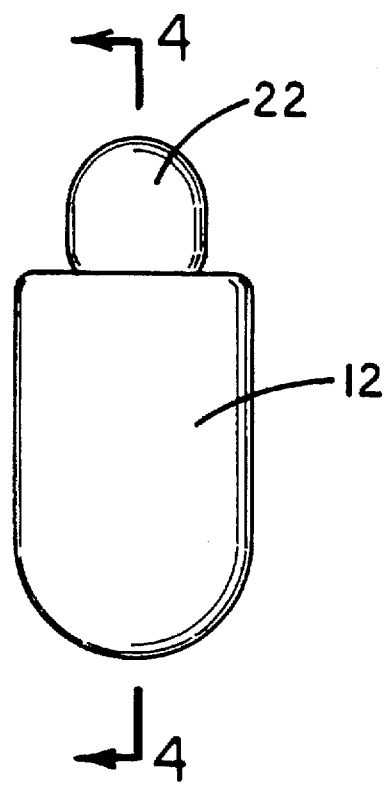
FIG. 3 is a side view of the present invention.

With reference now to the drawings, and in particular to FIGS. 1 through 4 thereof, a meat product pet medicine capsule embodying the principles and concepts of the present invention and generally designated by the reference numeral 10 will be described.

Figure 4:
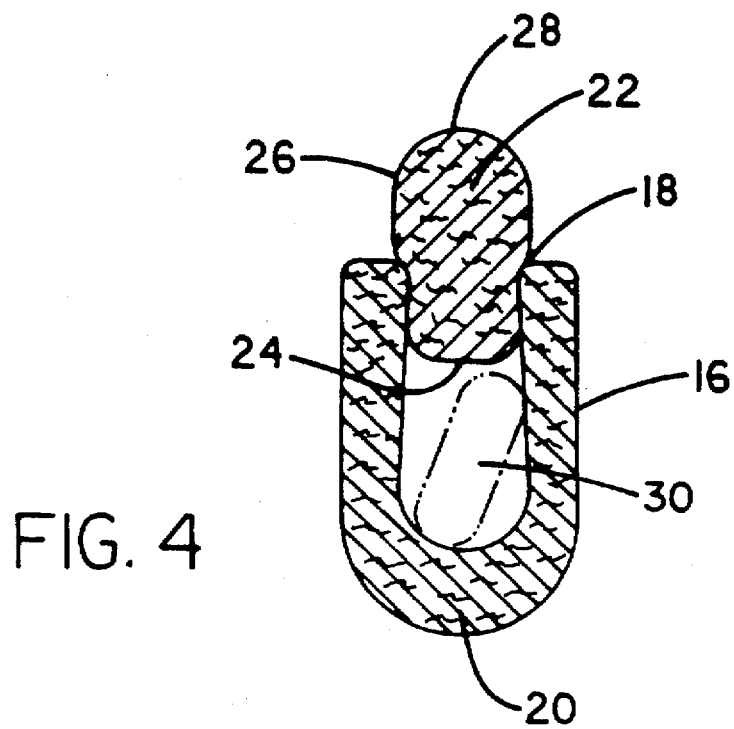
FIG. 4 is a cross-sectional view of the present invention taken along line 4—4 shown in FIG. 3.

The present invention, designated as numeral 10, includes a vial 12 constructed entirely of an edible semi-rigid meat product. The vial has an upper extent 16 with a hollow cylindrical configuration. As shown in FIG. 4, the vial includes a circular open top 18 of a first diameter. Further, a lower extent 20 of the vial is defined by a portion of a hollow sphere. The lower extent is integrally coupled in concentric relationship with the upper extent thus defining an interior space in communication with the open top. In the preferred embodiment, the height and width of the vial are equal and the length is three times the height and width. For example, the vial may have a height of ½ of an inch, a length of 1 and ½ inches and a width of ½ of an inch.

Next provided is a cap 22 constructed entirely of the edible semi-rigid meat product, similar to the vial. Preferably, such meat product is real beef jerky. The cap has a bottom 24 with a solid cylindrical configuration having the first diameter. An intermediate portion 26 of the cap is equipped with a solid cylindrical configuration and is integrally coupled in coaxial alignment with the bottom. The intermediate extent has a second diameter greater than the first diameter. A top 28 defined by a portion of a solid sphere with the second diameter is integrally coupled to intermediate extent. The cap preferably has a length which is about ⅓ the length of the vial.

Finally, a medicine capsule 30 is provided with a generally oval shape. The medicine is adapted to be situated within the interior space of the vial. Thereafter, the bottom of the cap is secured within the open top for sealing the medicine capsule therein. When secured, the cap provides a waterproof seal. It should be noted that the vial and cap combination are also ideal for containing medicines in both powder and liquid form.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A hollowed pet treat for medicating a pet comprising, in combination:

a vial formed entirely of edible semi-rigid meat and having an upper extent with a hollow cylindrical configuration including a circular open top of a first diameter and a lower extent defined by a portion of a hollow sphere which is integrally coupled in concentric relationship with the upper extent thereby defining an interior space in communication with the open top, wherein a height and a width of the vial are equal and a thickness of the lower extent is greater than that of the upper extent;

a cap adapted for being removably inserted in the open top of the upper extent of the vial for closing the interior space, the cap being formed entirely of edible semi-rigid meat and having a bottom with a solid cylindrical configuration having the first diameter, an intermediate portion with a solid cylindrical configuration integrally coupled in coaxial alignment with the bottom and having a second diameter greater than the first diameter and a top defined by a portion of a solid sphere having the second diameter and integrally coupled to intermediate extent; and a medicine capsule with a generally oval shape, the medicine is adapted to be situated within the interior space of the vial whereafter the bottom of the cap is secured within the open top for affording a waterproof seal to seal the medicine capsule therein.

* * * * *